United States Patent [19]

Scolastico et al.

[11] 4,220,798
[45] Sep. 2, 1980

[54] 19-METHYL-9-KETO-15-HYDROXY-PROST-18-ENOIC ACID DERIVATIVES AND PROCESS OF THEIR PREPARATION

[76] Inventors: Carol Scolastico, Via Vallisneri 13B, Milan, Italy; Giovanni Tronconi, Via 15 Martiri, Vimodrone (Milan), Italy

[21] Appl. No.: 58,677

[22] Filed: Jul. 18, 1979

Related U.S. Application Data

[62] Division of Ser. No. 830,315, Sep. 2, 1977.

[30] Foreign Application Priority Data

Sep. 7, 1976 [IT] Italy ............................... 26950 A/76

[51] Int. Cl.$^2$ ........................................... C07C 177/00
[52] U.S. Cl. ............................. 560/121; 260/390.9 P; 260/410.9 R; 260/413; 562/503; 424/305; 424/317

[58] Field of Search ....................... 560/121; 562/503; 260/410.9 R, 413

[56] References Cited

U.S. PATENT DOCUMENTS 3,932,479  1/1976  Bernady .......................... 260/448 A

FOREIGN PATENT DOCUMENTS 2635985  2/1978  Fed. Rep. of Germany .......... 560/121

Primary Examiner—Robert Gerstl
Attorney, Agent, or Firm—Haseltine, Lake & Waters

[57] ABSTRACT

The invention provides novel 19-methyl-9-keto-15-hydroxy-prost-18-enoic, -prosta-13,18-dienoic and -prosta-5,13,18-trienoic acids and esters having anti-ulcer and antiasthma activity.

8 Claims, No Drawings

19-METHYL-9-KETO-15-HYDROXY-PROST-18-ENOIC ACID DERIVATIVES AND PROCESS OF THEIR PREPARATION

This is a Rule 60 Division of U.S. patent application Ser. No. 830,315, filed Sept. 2, 1977.

The present invention relates to 19-methyl-9-keto-15-hydroxy-prost-18-enoic, 19-methyl-9-keto-15-hydroxy-prosta-13,18-dienoic and 19-methyl-9-keto-15-hydroxy-prosta-5,13,18-trienoic acid derivatives and to their esters. This invention relates also to a process for the preparation of such compounds.

The process of this invention comprises the reaction of the alkyl esters of 2-(ω-carboxy-y)-3-nitromethyl-cyclopentan-1-one (wherein y is a divalent rest, i.e. $-CH_2$-(a)-$(CH_2)_m$ where a is $-CH_2-CH_2-$ or

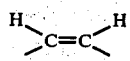

and m is an entire number between 2 and 4) with ethylene glycol, to transform the 1-carbonyl group into the corresponding ketal and, subsequently, said ketal into 2-(ω-carboxy-y)-3-formylcyclopentan-1-one-1-ethyleneketal.

The reaction of the aldehyde with a phosphonate sodium derivative of general formula

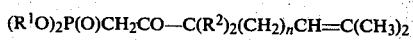

(wherein $R^1$ is a $C_1$-$C_3$-alkyl group of 1 to 3 carbon atoms, n is an entire number between 1 and 4 and $R^2$ may be H or $CH_3$), yields the corresponding derivatives of the 2-(ω-carboxy-y)-3-(3-ketoalcadienyl)-cyclopentan-1-one-1-ethyleneketal, the oxo-group of which in 15-position may be selectively reduced to alcohol. The hydrolysis of the ketal group yields the corresponding carbonyl group. If (a) represents $-CH_2-CH_2-$, the double bond in 13-position may be selectively reduced to a single bond by catalytic hydrogenation, whereas, if (a) represents

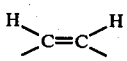

The conjugation with the carbonyl group in 15-position must be utilized to obtain the selective reduction of the 13-double bond.

The 13,14-dihydroderivatives having a carbonyl group in 15-position and (a)=

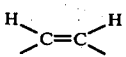

or $-CH_2-CH_2-$ may be reduced to the corresponding 15-alcohols by treatment with metal borohydrides; alternatively, they may be transformed into the corresponding tertiary alcohols through the reaction of the 15-carbonyl group with a Grignard's reagent $R^3MgX$, wherein X is a halogen atom and $R^3$ is an alkyl group of 1 to 3 carbon atoms.

The 19-methyl-9-keto-15-hydroxy-prost-18-enoic acid derivatives are endowed with biologic activity of prostaglandinic kind.

The prostanoic acids are obtained, according to this invention, through the conjugated addition of nitromethane to the 2-(ω-carboxy-y)-cyclopent-2-en-1-ones (1) (which are prepared by the method of A. S. C. Prakasa, U. R. Nayak, Synthesis 9, 608 (1975) if (a) represents $-CH_2-CH_2-$ whereas, if (a) represents

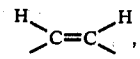

they are prepared by the method of P. A. Grieco, J. J. Reap, J.O.C., 38, 3413 (1973); said addition allows the preparation on technical scale. Such method is described in U.S. Pat. No. 3,773,795, but the process according to the present invention is different from the one mentioned above because the carbonyl group is protected in the form of ethylene ketal before transformation of the nitromethyl group into aldehyde. Said protective group is not removed in the course of the transformation $CH_2NO_2 \rightarrow CHO$, with the advantage that the product which is obtained after the Wittig condensation, the 9-carbonyl group of which is protected, is more suitable for the functional modifications which are to be made on the 15-carbonyl group.

The 2-(ω-carboxy-y)-3-nitromethyl-cyclopentan-1-ones (2) (wherein R represents a lower alkyl group) are transformed into the corresponding ketals (3) (R=lower alkyl group) by reaction with ethylene glycol and para-toluenesulphonic acid in benzene solution; subsequently, the nitromethyl group may be converted into an aldehyde (4) (R=lower alkyl) by reaction with $TiCl_3$ in aqueous solution at pH 5.

The so obtained raw 3-formyl-2-(ω-carboxy-y)-cyclopentan-1-one-1-ethyleneketal (4) (R=lower alkyl) may be used for the subsequent Wittig condensation by treatment at a temperature from $-30°$ to $+20°$ C. with the sodium phosphonate of a reagent of general formula

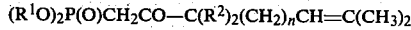

(wherein $R^1$ represents $C_1$-$C_3$-alkyl group, $R^2$ represents H or $CH_3$ and n is an entire number between 1 and 4), i.e. a dimethyl 2-ketoalkenylphosphonate, in the presence of an alkali metal hydride, preferably sodium hydride, and in an aprotic solvent, preferably 1,2-dimethoxyethane. (With the term "lower alkyl" are meant straight line or branched alkyl groups containing 1 to 3 carbon atoms, or straight chain alkyl groups containing 4 to 6 carbon atoms, including methyl, ethyl, propyl, butyl, pentyl and hexyl).

By dilution with water, extraction with a hydroun-mixable solvent, preferably diethyl ether, followed by washing, drying and evaporation of the solvent, the corresponding ester of a 2-(ω-carboxy-y)-3-(3-ketoalkadienyl)-cyclopentan-1-one-1-ethyleneketal is obtained of the general formula (5) (wherein R represents a lower alkyl, $R^2$ represents H or $CH_3$, n is an entire number between 1 and 4, m is an entire number between 2 and 4, (a) represents $-CH_2-CH_2-$ or $-CH=CH-$).

The compound of general formula (6) or the corresponding sodium salt (R=Na) may be reduced with an alkali metal borohydride, preferably $NaBH_4$, to the corresponding 2-(ω-carboxy-y)-3-(3-hydroxyalkadienyl)cyclopentan-1-one-ethyleneketal of formula (6). After hydrolysis of the protective group with 65% acetic acid the alcohol (7) is obtained (R=lower alkyl)

which, if $R^2$ represents an alkyl group, can be separated, by chromatography on $SiO_2$, in the alcohols (7a) and (7b). After hydrolysis with NaOH in aqueous methanol, the corresponding acids (7a; R=H), (7b; R=H) are obtained.

When the starting material employed in the above-described reaction sequence is the methyl ester of the 3-formyl-2-(6-carboxyhexyl)cyclopentan-1-one, and the employed reagent $C-(CH_3)_2$, then the compound of general formula (7), wherein (a) is $-CH_2-CH_2-$, m=3, R=$CH_3$, $R^2$=H and n=1, is the methyl 19-methyl-9-keto-15-hydroxyprosta-13,18-dienoate.

The double bond of the compounds of general formula (5) wherein (a) is $-CH_2-CH_2-$ may be selectively reduced to a single bond by catalytic reduction in the presence of a noble metal, for instance Pd/C 5%, in ethyl acetate or, preferably, of nichel Raney in ethanol, to yield compounds of general formula (8) (wherein (a) is $-CH_2-CH_2-$, R is a lower alkyl, n is an entire number between 1 and 4, $R^2$ is H or $CH_3$ and m is an entire number between 2 and 4).

When (a) in the compounds of formula (5) represents

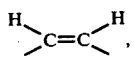

the selective reduction of the conjugated double bond is carried out in methanol solution, in the presence of $Fe(CO)_5$ and NaOH, as described by R. Noyori, I. Umeda, T. Ishigami, J.O.C. 37; 1542 (1972), to yield compounds of general formula (8), wherein (a) = 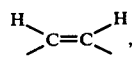

R=lower alkyl, $R^2$=$CH_3$ or H, n is an entire number between 1 and 4 and m is an entire number between 2 and 4.

The carbonyl group in 15-position of the compound of formula (8) may be selectively reduced to alcohol employing metal borohydrides in accordance with the above-described technique for the 13,14-unsaturated compounds. After hydrolysis with 65% acetic acid, compounds of general formula (9) are obtained (wherein R, (a), n and m have the above-described meaning) which may be then separated by chromatography in the alcohols (9a) and (9b). The hydrolysis with sodium hydroxide in aqueous methanol leads to the corresponding acids (9a; R=H), (9b; R=H).

The compounds of general formula (8), wherein (a) may be $-CH_2-CH_2-$, or

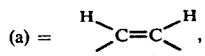

whereas R, $R^2$, n and m have the above-mentioned meanings, may be transformed into tertiary alcohols of general formula (10) by reaction with a stoichiometric quantity of the Grignard's reagent $R^3MgX$, wherein X is a halogen atom and $R^3$ is a $C_1$–$C_3$-alkyl group, in an inert solvent, preferably diethyl ether.

At the end of the reaction, the ketal (10) can be hydrolysed with 65% acetic acid to yield tertiary alcohols of general formula (11) in the form of esters (R=lower alkyl) or, after alkaline hydrolysis carried out with NaOH in methanol, the corresponding tertiary alcohols in the form of acids (11) (R=H).

The compounds of general formula (5) (wherein (a) represents $-CH_2-CH_2-$ or

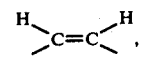

whereas R, $R^2$ and m have the above-mentioned meaning) may be converted in tertiary alcohols of general formula (12) by treatment with stoichiometric quantity of the Grignard's reagent $R^3MgX$ (wherein X is a halogen atom and $R^3$ is a $C_1$–$C_3$ lower alkyl group) in an inert solvent, preferably diethyl ether. After hydrolysis of the ketal function with 65% acetic acid, tertiary alcohols of general formula (13) (R=lower alkyl) are obtained, which, by hydrolysis with methanolic soda, yield the corresponding acids of general formula (13) (R=H).

The wavy lines in the formulae (10), (11), (12) and (13) mean that the steric relation of the hydroxy group and of the $R^3$-group with respect to the rest of the molecule is unknown.

For instance, when (a) is

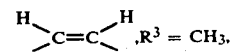

$R=R^2=H$, n=1, m=3, the 15,19-dimethyl-9-keto-15-hydroxyprosta-5,18-dienoic acid is obtained.

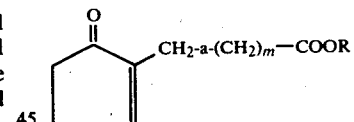

(1)

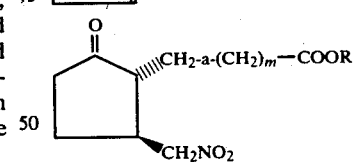

(2)

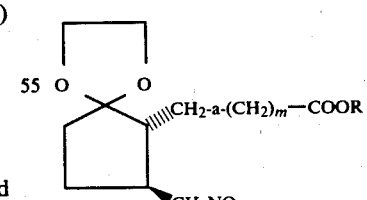

(3)

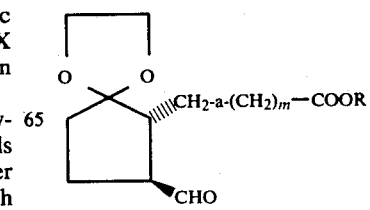

(4)

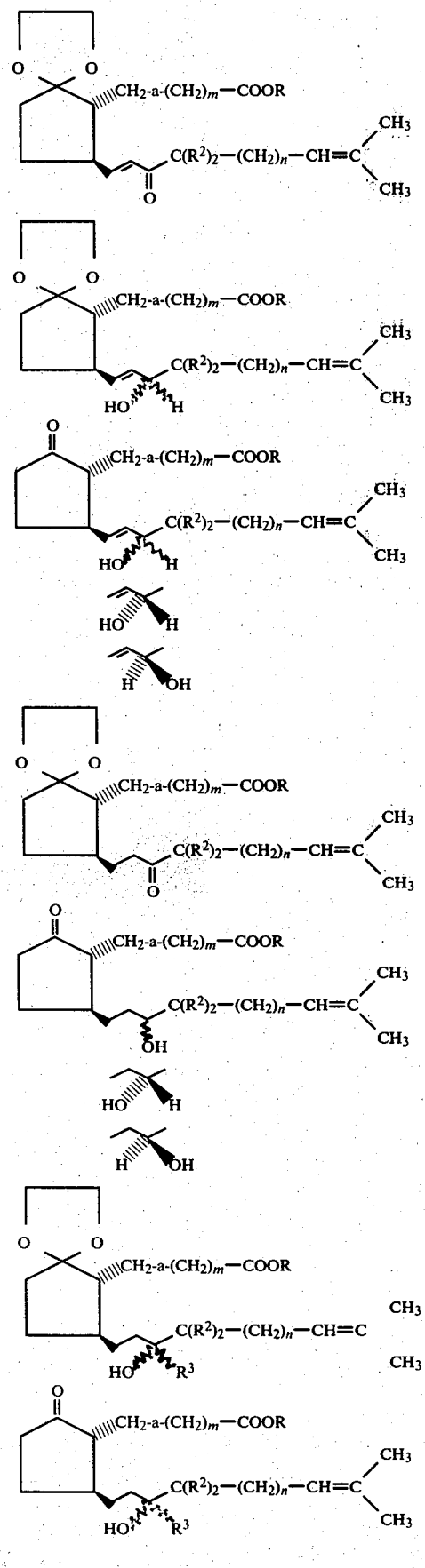
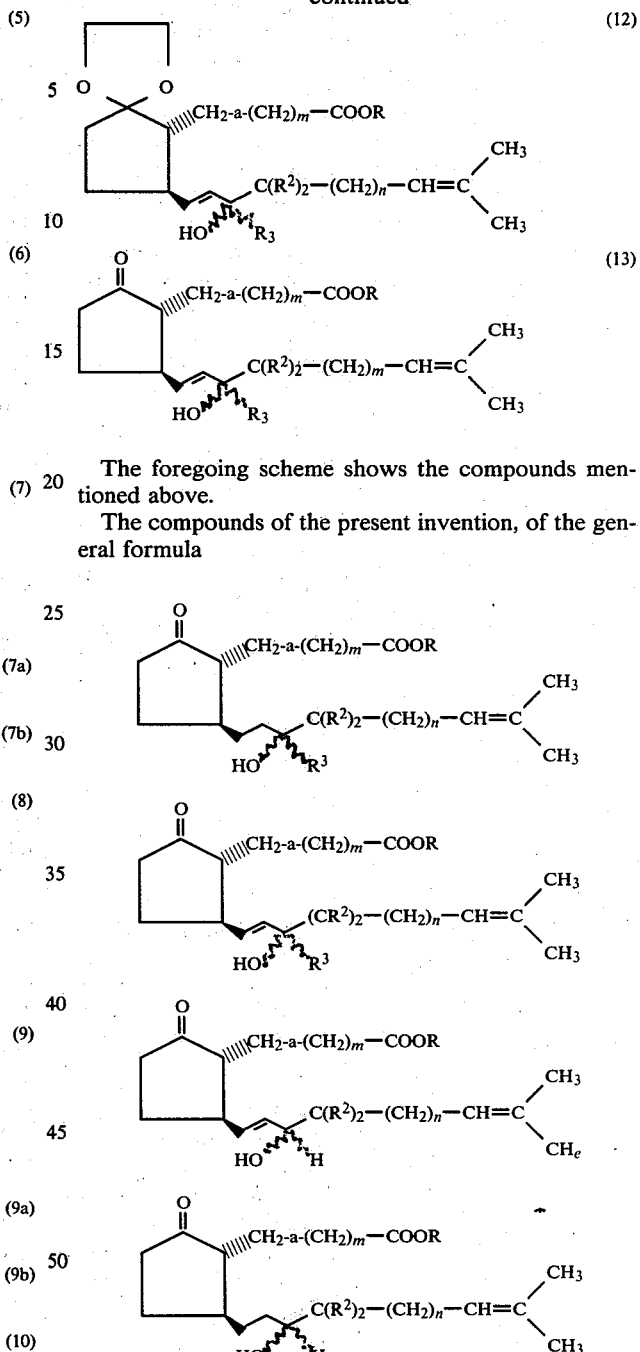

The foregoing scheme shows the compounds mentioned above.

The compounds of the present invention, of the general formula

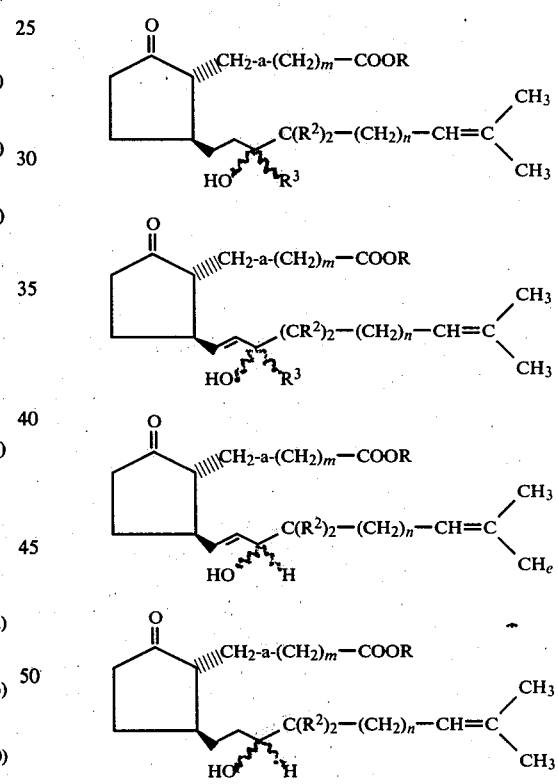

wherein R=H or lower alkyl group; $R_2$=H or $CH_3$, $R_3$=$C_1$-$C_3$ alkyl group, m=2,3, or 4, n=1,2,3 or 4, a=—CH=CH— or —$CH_2$—$CH_2$—, have interesting pharmacological properties.

Particularly, it has been found that they are endowed with valuable properties in the treatment of patological conditions associated with an excessive gastric secretion, as it is the case of the peptic ulcer, and the treatment of asthma.

It was found that the compounds of this invention, if administered to rats, with the test described by Shay et al. in Gastroenterology, 26, 906 (1954), inhibit the secretion of gastric acid and are therefore useful as antisecretory agents. Furthermore, said compounds, if administered to rats with the test described by Armitage et al. in British J. Pharmacol., 16, 59 (1961) releave the bronchospasmus and are therefore useful as bronchospasmolitics.

When the compounds of the present invention are employed as antisecretory agents in warm-blooded animals, for instance cats or rats, their corresponding doses are determined by their solubility, by the selected administration way and by the "Standard Biological Practice". They may be administered orally, for instance in form of tablets containing excipients as starch, lactose, sacharose, some kinds of kaolin, flavour agents and so on. However, they may be administered preferably in the form of solutions which may also comprise other compounds, such as NaCl or glucose, in such quantities to make the solution isotonic.

As bronchospasmolitic agents the compounds of the present invention are preferably administered in the form of an aerosol. The doses of such antisecretory agents will vary with the administration forms and the particular hosts.

Generally, the compounds of this invention are administered in such a concentration as to obtain efficient results without causing damages or undesidered secondary effects, preferably in a dose between 0.1 mg/kg up to 10 mg/kg, although there may be some variations. To obtain good results, a dosage between 0.5 mg/kg and 5 mg/kg is preferably employed.

The invention will be illustrated by the following experimental examples, which, however, in no way limit its range.

EXAMPLE I (a) Dimethyl (6-methyl-hept-5-en-2-one-phosphonate

To a solution of dimethyl methylphosphonate (36 g.) in anhydrous tetrahydrofurane (260 ml.), cooled to $-74°$ C. and under nitrogen, 132 ml. of n-butyllithium (2.2 N in hexane) are added. After 15 minutes, 20 g of methyl 5-methyl-4-hexenoate are added. The reaction mixture is stirred at $-74°$ C. for 60 minutes, then the temperature is allowed to rise spontaneously to 0° C. The mixture is diluted with water (390 ml.), the tetrahydrofurane is evaporated in vacuo and the aqueous phase is extracted with $CH_2Cl_2$ (4×150 ml.). The organic layer is washed with water to neutrality, dehydrated over sodium sulphate and the solvent evaporated in vacuo. The residue is distilled under reduced pressure, to yield 20 g. of dimethyl (6-methyl-hept-5-en-2-one)-phosphonate.

B.p. = 128–130 at 0.5 mm Of Hg.
For $C_{10}H_{19}O_4P$—calculated: C=51.24; H=8.18; P=13.25; found: C=51.19; H=8.12; P=13.29.

(b) Dimethyl (3,3,6-trimethyl-hept-5-en-2-one)-phosphonate

As described in Example 1(a), from 12.5 g. of dimethyl methylphosphonate, 43 ml. of n-butyllithium (2,2 N in hexane), 90 ml. of anhydrous tetrahydrofurane, 8 g. of methyl 2,2,5-trimethyl-4-hexenoate, 6 g. of dimethyl (3,3,6-trimethyl-hept-5-en-2-one)-phosphonate are obtained.

B.p. = 127°–130° C. at 0.3 mm of Hg.
For $C_{12}H_{23}O_4P$—calculated: C=54.92; H=8.84; P=11.83; found: C=54.86; H=8.76; P=11.91.

(c) 2-(6-Carboxyhexyl)-3-nitromethyl-cyclopentan-1-one, methyl ester

The solution of 2-(6-carboxyhexyl)-cyclopent-2-en-1-one methyl ester (5.4 g.), nitromethane (5.4 ml.), N,N,N', N'-tetramethylguanidine (0.32 ml.) is left for 18 hours at room temperature. The mixture is washed with HCl 3 N and the organic layer is separated. The aqueous phase is then extracted with diethyl ether (4×20 ml.) and the ethereal extracts are added to the abovementioned organic layer. The so obtained solution is washed with water to neutrality, dried over sodium sulphate and the solvent is removed in vacuo. From the oily residue, by chromatography on silica (120 g.) and elution with benzine/ethyl acetate (4:1), 4.8 g. of pure 2-(6-carboxyhexyl)-3-nitromethyl-cyclopentan-1-one methyl ester are obtained.

oil, $\nu_{max}^{film}$: 1745, 1555 cm$^{-1}$
N.M.R. ($\delta$; $CDCl_3$): 3.63 3H, s, $OCH_3$); 4.22–4.80 (2H, m, $CH_2NO_2$).

By the same method, from 2-(methyl cis-hept-2-en-7-oate)-cyclopent-2-en-1-one, the 2-(methyl cis-hept-2-en-7-oate)-3-nitromethyl-cyclopentan-1-one is obtained.

oil, $\nu_{max}^{film}$: 1740, 1555 cm$^{-1}$;
N.M.R. ($\delta$; $CDCl_3$): 3.64 (3H, s, $OCH_3$); 4.14–4.87 (2H, m, $-CH_2NO_2$); 5.05–5.75 (2H, m, cis CH=CH).

(d) 1-Ethylenedioxy-2-(6-carboxyhexyl)-3-nitromethyl-cyclopentane, methyl ester

The solution of 2-(6-carboxyhexyl)-3-nitromethyl-cyclopentan-1-one, methyl ester (14 g.) in benzene (200 ml.), ethylene glycol (16.1 ml.), p-toluenesulphonic acid (0.315 g.), is heated to boiling for 16 hours. The reaction water is separated in a Marcusson apparatus. The mixture is washed with an aqueous saturated $NaHCO_3$-solution (50 ml.), then with water to neutrality, dried over sodium sulphate and the solvent is evaporated in vacuo. From the oily residue, by chromatography on silica (300 g.) and elution with benzene/ethyl acetate (6:1), 13 g. of 1-ethylenedioxy-2-(6-carboxyhexyl)-3-nitromethyl-cyclopentane, methyl ester, are obtained.

oil, $\nu_{max}^{film}$: 1740, 1555 cm$^{-1}$.
N.M.R. ($\delta$; $CDCl_3$): 3.64 (3H, s, $OCH_3$); 3.88 (4H, s, $-O-CH_2-CH_2-O-$); 4.06–4.68 (2H, m, $CH_2NO_2$).

By the same method, from 2-(methyl cis-hept-2-en-7-oate)-3-nitromethyl-cyclopentan-1-one, the 1-ethylenedioxy-2-(methyl cis-hept-2-en-7-oate)-3-nitromethyl-cyclopentane is prepared.

oil, $\nu_{max}^{film}$: 1740, 1550 cm$^{-1}$.
N.M.R. ($\delta$; $CDCl_3$): 3.62 (3H, s, $-CH_3$); 3.85 (4H, s, $-O-CH_2-CH_2-O-$); 3.98–4.70 (2H, m, $-CH_2NO_2$); 5.23–5.50 (2H, m, cis CH=CH).

(e) 1-Ethylenedioxy-2-(6-carboxyhexyl)-3-formyl-cyclopentane, methyl ester

To the solution of 0.82 g. of sodium in 72 ml. of anhydrous methanol, at 10° C. and under nitrogen, a solution of 1-ethylenedioxy-2-(6-carboxyhexyl)-3-nitromethyl-cyclopentane, methyl ester (10.7 g.) in anhydrous methanol (72 ml.) is added, drop by drop. After stirring for 15 minutes at room temperature, the solution of ammonium acetate (65.5 g.), $TiCl_3$ 15% (118 ml.), $H_2O$ (214 ml.) is rapidly added, and the mixture is stirred for 50 minutes under nitrogen, then extracted with diethyl ether (3×200 ml.). The organic layer is washed with a saturated solution of NaHCO$_3$ in water, then with water to neutrality.

After drying over Na$_2$SO$_4$, the solvent is evaporated in vacuo, yielding 8.2 g. of an oily residue, which is used as such for the Wittig reaction.

oil $\nu_{max}^{film}$: 2710, 1735 cm$^{-1}$.

By the same method, starting from 1-ethylenedioxy-2-(methyl cis-hept-2-en-7-oate)-3-nitromethyl-cyclopentane, the 1-ethylenedioxy-2-(methyl cis-hept-2-en-7-oate)-3-formyl-cyclopentane is obtained.

oil $\nu_{max}^{film}$: 2710, 1730 cm$^{-1}$.

N.M.R. ($\delta$; CDCl$_3$): 3.65 (s, 3H, —OCH$_3$); 3.88 (4H, s, —O—CH$_2$—CH$_2$—O—); 5.25–5.60 (2H, m, cis CH═CH); 9.50–9.65 (1H, d, CHO).

(f)
9-Ethylenedioxy-15-keto-16,16,19-trimethyl-prosta-13,18-dienoic acid, methyl ester At $-35°$ C., 0.82 g. of a suspension of NaH 50% in mineral oil is added to a solution of dimethyl (3,3,6-trimethyl-hept-5-en-2-one) phosphonate (4.5 g.), 1-ethylenedioxy-2-(6-carboxyhexyl)-3-formyl-cyclopentane methyl ester (4.85 g.) in anhydrous 1,2-dimethoxyethane (150 ml.): the freezing bath is removed and the mixture is stirred for 3 hours under nitrogen. (The mixture reaches the room temperature in about 1 hour). After cautious addition of 1 ml of methanol, the mixture is poured on icy water (200 ml.), then extracted with diethyl ether (2×70 ml). The ethereal extract is washed with water to neutrality, dried on Na$_2$SO$_4$ and the solvent evaporated in vacuo. The oily residue (8 g.) is purified by chromatography on SiO$_2$ (200 g.). By elution with hexane/ethyl acetate (2:1), 4.5 g. of 9-ethylenedioxy-15-keto-16,16,19-trimethyl-prosta-13,18-dienoic acid, methyl ester, are obtained.

oil$_{max}^{film}$: 1745, 1690, 1625 cm$^{-1}$.

N.M.R. ($\delta$; CDCl$_3$): 1.09 (6H, s, 2(CH$_3$)-C$_{16}$); 1.58 (3H, broad singlet, CH$_3$-C$_{19}$); 1.67 (3H, broad singlet, CH$_3$-C$_{19}$); 3.62 (3H, s, —OCH$_3$); 3.88 (4H, s, —O—CH$_2$—CH$_2$—O); 4.80–5.18 (1H, m, C$_{18}$-H); 6.45 (1H, d=15 cps, C$_{14}$-H); 6.82 (1H,dd, J=15 cps, J=7.5 cps, C$_{13}$-H).

By the same method the following compounds are prepared:

1. 9-Ethylenedioxy-15-keto-19-methyl-prosta-13,18-dienoic acid, methyl ester, starting from the sodium derivative of dimethyl (6-methyl-hept-5-en-2-one)-phosphonate.

oil $\nu_{max}^{film}$: 1745, 1675, 1630 cm$^{-1}$.

N.M.R. ($\delta$; CDCl$_3$): 1.63 (3H, broad singlet, CH$_3$-C$_{19}$); 1.68 (3H, broad singlet, CH$_3$-C$_{19}$); 3.63 (3H, s, —OCH$_3$); 3.87 (4H, s, —C—CH$_2$—CH$_2$—O—); 4.90–5.30 (1H, m, C$_{18}$-H); 6.04 (d, J=15.5 cps, C$_{14}$-H); 6.71 (dd, J=15.5 cps, J=8 cps, C$_{13}$-H).

2. 9-Ethylenedioxy-15-keto-16,16,19-trimethyl-prosta-5cis,13-trans,18-trienoic acid, methyl ester, starting from 1-ethylenedioxy-2-(methyl cis-hept-2-en-7-oate)-3-formyl-cyclopentane and from the sodium derivative of dimethyl (3,3,6-trimethyl-hept-5-en-2-one)-phosphonate.

oil, $\nu_{max}^{film}$: 1745, 1690, 1625 cm$^{-1}$.

N.M.R. ($\delta$; CDCl$_3$): 1.05 (3H, s, CH$_3$-C$_{16}$); 1.08 (3H, s, CH$_3$-C$_{16}$); 1.58 (3H, broad singlet, CH$_3$-C$_{19}$); 1.62 (3H, broad singlet, CH$_3$-C$_{19}$); 3.63 (3H,s,OCH$_3$); 3.87 (4H, s, —OCH$_2$—CH$_2$O); 4.77–5.18 (1H, m, C$_{18}$-H); 5.18–5.50 (2H, m, cis —CH═CH—); 6.44 (1H, d, J═15 cps, C$_{14}$-H); 6.80 (1H, dd, J=15 cps, J=7.5 cps, C$_{13}$-H).

3. 9-Ethylenedioxy-15-keto-19-methyl-prosta-5cis,13-trans,18-trienoic acid, methyl ester, starting from 1-ethylenedioxy-2-(methyl cis-hept-2-en-7-oate)-3-formyl-cyclopentane and from the sodium derivative of dimethyl(6-methyl-hept-5-en-2-one)phosphonate.

oil, $\nu_{max}^{film}$: 1740, 1675, 1630 cm$^{-1}$.

N.M.R. ($\delta$; CDCl$_3$): 1.63 (3H, broad singlet, CH$_3$-C$_{19}$); 1.67 (3H, broad singlet, CH$_3$-C$_{19}$); 3.63 (3H, s, —OCH$_3$); 3.86 (4H, s, —O—CH$_2$—CH$_2$—O—); 4.90–5.50 (3H, m, C$_{18}$-H, cis —CH═CH—); 6.05 (1H, d, J=16 cps, C$_{14}$-H); 6.66 (1H, dd, J=16 cps, J=8 cps, C$_{13}$-H).

(g)
9-keto-15-hydroxy-16,16,19-trimethyl-prosta-13,18-dienoic acid, methyl ester To a solution of 9-ethylenedioxy-15-keto-16,16,19-trimethyl-prosta-13,18-dienoic acid, methyl ester, (5.2 g.) in methanol (40 ml.), 0.89 g of sodium borohydride are gradually added, while the temperature is kept under 35° C. The mixture is stirred for 30 minutes, then diluted with 300 ml. of water and extracted with ethyl acetate (3×100 ml). The organic layer is washed with water to neutrality, dried over Na$_2$SO$_4$ and the solvent is evaporated in vacuo, to obtain a residue (4.9 g) which is suspended in acetic acid 65% (60 ml.) and stirred at room temperature for 60 minutes. The so obtained solution is diluted with water (200 ml.) and extracted with diethyl ether (3×100 ml). The organic phase is washed with an aqueous, saturated solution of NaHCO$_3$, then with water to neutrality, dried over Na$_2$SO$_4$, and the solvent is evaporated in vacuo. The oily residue (4.2 g. is purified by chromatography on SiO$_2$ (400 g.); the eluent is benzene/ethyl acetate (4:1). One gram of 9-keto-15$\beta$-hydroxy-16,16,19-trimethyl-prosta-13,18-dienoic acid, methyl ester, 0.5 g. of 9-keto-15$\alpha$-hydroxy-16,16,19-trimethyl-prosta-13,18-dienoic acid, methyl ester, and 2.1 g. of a mixture of 15$\alpha$- and 15$\beta$-isomers are obtained.

(15$\beta$)oil:$\nu_{max}^{film}$: 3510, 1745 cm$^{-1}$.

N.M.R. ($\delta$; CDCl$_3$): 0.82 (3H, s, CH$_3$-C$_{16}$); 0.84 (3H, s, CH$_3$-C$_{16}$); 1.62 (3H, broad singlet, CH$_3$-C$_{19}$); 1.72 (3H, broad singlet, CH$_3$-C$_{19}$); 3.64 (3H, s, —OCH$_3$); 3.73–3.95 (1H, m, C$_{15}$-H); 5.05–5.45 (1H, m, C$_{18}$-H); 5.58–5.77 (2H, m, trans CH═CH)

(15$\alpha$)oil:$\nu_{max}^{film}$: 3505, 1745 cm$^{-1}$.

N.M.R. ($\delta$; CDCl$_3$): 0.83 (3H, s, CH$_3$-C$_{16}$); 0.87 (3H, s, —CH$_3$-C$_{16}$); 1.62 (3H, broad singlet, CH$_3$-C$_{19}$); 1.72 (3H, broad singlet, CH$_3$-C$_{19}$); 3.64 (3H, s, —OCH$_3$); 3.75–3.92 (1H, m, C$_{15}$-H); 4.95–5.40 (1H, m, C$_{18}$-H); 5.56–5.74 (2H, m, trans CH═CH).

By the same method the following compounds are prepared:

1. From 9-ethylenedioxy-15-keto-19-methyl-prosta-13,18-dienoic acid, methyl ester, the 9-keto-15-hydroxy-19-methyl-prosta-13,18-dienoic acid, methyl ester is obtained.

oil, $\nu_{max}^{film}$: 3460, 1740 cm$^{-1}$.

N.M.R. ($\delta$; CDCl$_3$): 1.62 (3H, broad singlet, C$_{19}$-CH$_3$); 1.69 (3H, broad singlet, C$_{19}$-CH$_3$), 3.64 (3H, s, —OCH$_3$); 3.98–4.24 (1H, m, C$_{15}$-H); 5.02–5.30 ((1H, m, C$_{18}$-H); 5.52–5.62 (1H, m, trans CH═CH).

2. From 9-ethylenedioxy-15-keto-16,16,19-trimethyl-prosta-5-cis,13-trans,18-trienoic acid, methyl ester, the 9-keto-15$\alpha$-hydroxy-16,16,19-trimethyl-prosta-5-cis,13-trans,18-trienoic acid, methyl ester is obtained.

oil, $\nu_{max}^{film}$: 3510, 1740 cm$^{-1}$.

N.M.R. ($\delta$; CDCl$_3$): 0.86 (3H, s, CH$_3$-C$_{16}$); 0.88 (3H, s, CH$_3$-C$_{16}$); 1.64 (3H, broad singlet, CH$_3$-C$_{19}$); 1.74 (3H, broad singlet, CH$_3$-C$_{19}$); 3.65 (3H, s, —OCH$_3$);

3.76–3.95 (1H, m, C$_{15}$-H); 5.00–5.50 (3H, m, C$_{18}$-H, cis—CH=CH—); 5.58–5.75 (2H, m, trans—CH=CH—).

3. From 9-ethylenedioxy-15-keto-16,16,19-trimethyl-prosta-5-cis,13-trans,18-trienoic acid, methyl ester, the 9-keto-15β-hydroxy-16,16,19-trimethyl-prosta-5-cis,13-trans,18-trienoic acid, methyl ester is obtained.

oil, $\nu_{max}^{film}$: 3510, 1740 cm$^{-1}$.

N.M.R. (δ; CDCl$_3$); 0.85 (3H,s,CH$_3$-C$_{16}$); 0.89 (3H,s,CH$_3$-C$_{16}$); 1.64 (3H, broad singlet, CH$_3$-C$_{19}$); 1.74 (3H,broad singlet, CH$_3$-C$_{19}$); 3.65 (3H,s, —OCH$_3$); 3.72–3.94 (1H,m, C$_{15}$-H); 5.02–5.54 (3H, m, C$_{18}$-H,cis—CH=CH—); 5.58–5.78 (2H,m,trans—CH=CH—).

EXAMPLE II (a) 9-Ethylenedioxy-15-keto-19-methyl-prost-18-enoic acid, methyl ester Method A To the solution of 4.4 g of 9-ethylenedioxy-15-keto-19-methyl-prost-13,18-dienoic acid, methyl ester, in ethanol (60 ml.) are added 0.8 g of Raney-nickel washed with ethanol and the mixture is hydrogenated at room temperature under pressure. After absorption of the theoretical quantity of hydrogen the catalyzer is separated by filtration and the solvent evaporated in vacuo, to yield 3.9 g of 9-ethylenedioxy-15-keto-19-methyl-prost-18-enoic acid, methyl ester.

Method B

To the solution of 3.6 g of 9-ethylenedioxy-15-keto-19-methyl-prost-13,18-dienoic acid, methyl ester, in ethyl acetate (100 ml.) 0.18 g of Pd/C (5%) are added and the mixture is hydrogenated at room temperature under pressure. After absorption of the theoretical quantity of hydrogen the catalyzer is separated by filtration and the solvent evaporated in vacuo to yield 3.4 g of 9-ethylenedioxy-15-keto-19-methyl-prost-18-enoic acid, methyl ester.

oil: $\nu_{max}^{film}$ 1740, 1720 cm$^{-1}$.

N.M.R. (δ; CDCl$_3$): 1.61 (3H, broad singlet, CH$_3$-C$_{19}$); 1.67 (3H, broad singlet, CH$_3$-C$_{19}$); 3.64 (3H, s, —OCH$_3$); 3.88 (4H, s, —O—CH$_2$—CH$_2$—O—); 4.88–5.23 (1H, m, C$_{18}$-H).

By the same method, starting from 9-ethylenedioxy-15-keto-16,16,19-trimethyl-prosta-13,18-dienoic acid, methyl ester, the 9-ethylenedioxy-15-keto-16,16,19-trimethyl-prost-18-enoic acid, methyl ester is obtained.

oil $\nu_{max}^{film}$: 1745, 1710 cm$^{-1}$.

N.M.R. (δ; CDCl$_3$): 1.05 (3H, s, CH$_3$-C$_{16}$); 1.07 (3H, s, CH$_3$-C$_{16}$); 1.59 (3H, broad singlet, CH$_3$-C$_{19}$); 1.70 (3H, broad singlet, CH$_3$-C$_{19}$); 3.64 (3H, s, —OCH$_3$); 3.67 (4H, s, —O—CH$_2$—CH$_2$—O—); 4.82–5.18 (1H, m, C$_{18}$-H).

(b)
9-Ethylenedioxy-15-keto-19-methyl-prosta-5-cis,18-dienoic acid, methyl ester The mixture of Fe(CO)$_5$ (0.784 g), NaOH (80 mg) in 2 ml of methanol/water (95:5) is stirred for 10 minutes at room temperature under nitrogen. To the obtained solution are added 0.392 g of 9-ethylenedioxy-15-keto-19-methyl-prosta-5-cis,13-trans-18 trienoic acid, methyl ester, and the mixture is stirred for 48 hours at room temperature under nitrogen. The solvent is evaporated at reduced pressure; by chromatography on silica(15 g) and elution with benzine/ethyl acetate (9:3) 0.3 g of 9-ethylenedioxy-15-keto-19-methyl-prosta-5-cis,18-dienoic acid, methyl ester, are obtained.

oil, $\nu_{max}^{film}$: 1740, 1710, 1630 cm$^{-1}$.

N.M.R. (δ; CDCL$_3$): 1.62 (3H, broad singlet; CH$_3$-C=), 1.67 (3H, broad singlet,

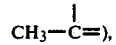

CH$_3$—C=), 3.65 (4H, s, —OCH$_2$CH$_2$O—), 3.85 (3H, s, —OCH$_3$), 4.85–5.25 (1H, m, —CH=C), 5.25–5.58 (2H, m, —CH=CH—).

(c)
9-Keto-15-hydroxy-16,16,19-trimethyl-prost-18-enoic acid, methyl ester

To the solution of 2.4 g of 9-ethylenedioxy-15-keto-16,16,19-trimethyl-prost-18-enoic acid, methyl ester in methanol (20 ml.) 0.4 g of sodium borohydride are gradually added while the temperature is kept under 35° C. The mixture is stirred for 30 minutes, then diluted with water (150 ml.) and extracted with ethyl acetate (3×70 ml.). The organic layer is washed with water to neutrality, dried over sodium sulphate and the solvent is removed in vacuo. The oily residue (2.2 g) is suspended in 65% acetic acid (30 ml.) and stirred at room temperature for 60 minutes. The obtained solution is diluted with water (100 ml.) and extracted with diethyl ether (3×70 ml). The organic layer is washed with aqueous saturated NaHCO$_3$ solution to neutrality, dried over sodium sulphate and the solvent is evaporated. From the oily residue (1.8 g), by chromatography on silica (200 g) and elution with benzene/ethyl acetate (4:1), 0.48 g of 9-keto-15β-hydroxy-16,16,19-trimethyl-prost-18-enoic acid, methyl ester, 0.40 g of 9-keto-15α-hydroxy-16,16,19-trimethyl-prost-18-enoic acid, methyl ester and 0.48 g of a mixture of 15α and 15β are obtained.

15α oil $\nu_{max}^{film}$: 3490, 1740 cm$^{-1}$.

N.M.R. (δ, CDCl$_3$): 0.85 (3H, s, CH$_3$-C$_{16}$), 0.87 (3H, s, CH$_3$-C$_{16}$); 1.62 (3H, broad singlet, CH$_3$-C$_{19}$); 1.73 (3H, broad singlet, CH$_3$-C$_{19}$); 8.18–3.45 (1H, m, C$_{15}$-H); 3.64 (3H, s, —OCH$_3$); 5.08–5.43 (1H, m, C$_{18}$-H).

15β oil $\nu_{max}^{film}$: 3500, 1740 cm$^{-1}$.

N.M.R. (δ; CDCl$_3$): 0.85 (3H, s, CH$_3$-C$_{16}$); 0.87 (3H, s, CH$_3$-C$_{16}$); 1.62 (3H, broad singlet, CH$_3$-C$_{19}$); 1.73 (3H, broad singlet, CH$_3$-C$_{19}$); 3.12–3.44 (1H, m, C$_{15}$-H); 3.64 (3H, s, —OCH$_3$); 5.05–5.45 (1H, m, C$_{18}$-H).

EXAMPLE III

9-Keto-15-hydroxy-15,19-dimethyl-prost-18-enoic acid, methyl ester

To the solution of 3.3 g of 9-ethylenedioxy-15-keto-19-methyl-prost-18-enoic acid, methyl ester (obtained as described in Example IIa) in diethyl ether (30 ml.) is added drop by drop in 30 minutes a solution of CH$_3$MgI (0.24 g of Mg, 0.6 ml of CH$_3$I, 30 ml of diethyl ether). After stirring for 30 minutes an aqueous saturated NH$_4$Cl-solution (15 ml.) is added and the stirring is continued until two clear phases are obtained. The organic layer is separated, washed with water to neutrality, dried over sodium sulphate and the solvent is evaporated in vacuo. The oily residue is suspended in acetic acid 65% (45 ml.) and stirred for 60 minutes at room temperature. The solution is then diluted with water (130 ml.) and extracted with diethyl ether (3×70 ml.); the organic layer is washed with an aqueous saturated NaHCO$_3$-solution, then with water to neutrality, dried over sodium sulphate and the solvent is evaporated in vacuo, obtaining 2.2 g of an oily residue. By chromatography on silica (90 g) and elution with hexane/ethyl acetate (2:1) 1.6 g of 9-keto-15-hydroxy-15,19-dimethyl-prost-18-enoic acid, methyl ester are obtained.

oil $\nu_{max}^{film}$: 3500, 1740 cm$^{-1}$.

N.M.R. ($\delta$; CDCl$_3$): 1.20 (3H, s, CH$_3$-C$_{15}$); 1.63 (3H, broad singlet, CH$_3$-C$_{19}$); 1.70 (3H, broad singlet, CH$_3$-C$_{19}$); 3.86 (3H, s, —OCH$_3$); 5.03-5.27 (1H, m, C$_{18}$-H)

By the same method are prepared:

(1) 9-Keto-15-hydroxy-15,19-dimethyl-prosta-13,18-dienoic acid, methyl ester starting from 9-ethylenedioxy-15-keto-19-methyl-prosta-13,18-dienoic acid, methyl ester.

oil $\nu_{max}^{film}$: 3460, 1740 cm$^{-1}$.

N.M.R. ($\delta$; CDCl$_3$): 1.30 (3H, s, CH$_3$-C$_{15}$); 1.62 (3H, s, CH$_3$-C$_{19}$); 1.70 (3H, s, CH$_3$-C$_{19}$); 3.66 (s, 3H, —OCH$_3$); 5.02-5.27 (1H, m, C$_{18}$-H); 5.65 (2H, d, J=3 cps, trans CH=CH).

(2) 9-Keto-15-hydroxy-15,19-dimethyl-prosta-5-cis,18-dienoic acid, methyl ester starting from 9-ethylenedioxy-15-keto-19-methyl-prosta-5-cis,18-dienoic acid, methyl ester.

oil $\nu_{max}^{film}$: 3500, 1740 cm$^{-1}$. N.M.R. ($\delta$; CDCl$_3$): 1.21 (3H, s, CH$_3$-C$_{15}$); 1.63 (3H, broad singlet, CH$_3$-C$_{19}$); 1.69 (3H, broad singlet, CH$_3$-C$_{19}$); 3.64 (3H, s, —OCH$_3$); 4.92-5.22 (1H, m, C$_{18}$-H); 5.23-5.48 (2H, m, cis—CH=CH—).

EXAMPLE IV

9-Keto-15-hydroxy-19-methyl-prosta-13,18-dienoic acid

The solution of 0.5 g of 9-keto-15-hydroxy-19-methyl-prosta-13,18-dienoic acid, methyl ester, 0.170 g of NaOH in water (1.5 ml), methanol (4.5 ml) is left for two hours at room temperature under nitrogen, then diluted with water (22 ml) and extracted with diethyl ether (10 ml). The aqueous layer is acidified (congo red) with HCl (5%), then extracted with diethyl ether (3×15 ml). The ethereal solution is washed with water to neutrality, dried over sodium sulphate and the solvent evaporated in vacuo to yield 0.44 g of 9-keto-15-hydroxy-19-methyl-prosta-13,18-dienoic acid (oil).

By the same method are prepared:

1. 9-Keto-15α-hydroxy-16,16,19-trimethyl-prosta-13,18-dienoic acid (oil which solidifies slowly)
2. 9-Keto-15β-hydroxy-16,16,19-trimethyl-prosta-13,18-dienoic acid (oil)
3. 9-Keto-15α-hydroxy-16,16,19-trimethyl-prost-18-enoic acid (oil)
4. 9-Keto-15β-hydroxy-16,16,19-trimethyl-prost-18-enoic acid (oil)
5. 9-Keto-15-hydroxy-15,19-dimethyl-prost-18-enoic acid (oil)
6. 9-Keto-15-hydroxy-15,19-dimethyl-prosta-13,18-dienoic acid (oil)
7. 9-Keto-15α-hydroxy-16,16,19-trimethyl-prosta-5-cis,13-trans,18-trienoic acid (oil)
8. 9-Keto-15β-hydroxy-16,16,19-trimethyl-prosta-5-cis,13-trans,18-trienoic acid (oil)
9. 9-Keto-15-hydroxy-15,19-dimethyl-prosta-5-cis,18-dienoic acid (oil).

We claim:

1. Compounds of the formula

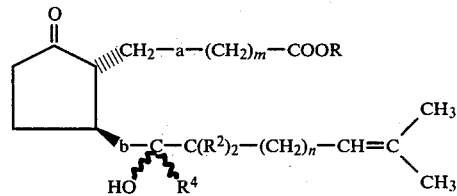

where
R is hydrogen or alkyl of 1 to 3 carbon atoms;
R$^2$ is hydrogen or methyl;
R$^4$ is hydrogen or alkyl of 1 to 3 carbon atoms;
m is 2, 3 or 4;
n is 1;
a is —CH$_2$—CH$_2$—;
b is —CH$_2$—CH$_2$—.

2. Compounds of the formula

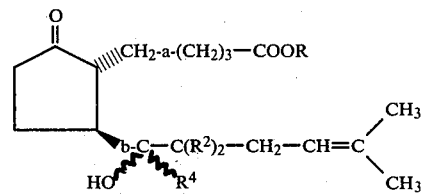

where
R is hydrogen or alkyl of 1 to 3 carbon atoms;
R$^2$ is hydrogen or methyl;
R$^4$ is hydrogen or alkyl of 1 to 3 carbon atoms;
a is —CH$_2$—CH$_2$—;
b is —CH$_2$—CH$_2$—.

3. A compound according to claim 2, which is 9-keto-15β-hydroxy-16,16,19-trimethyl-prost-18-enoic acid, methyl ester.

4. A compound according to claim 2, which is 9-keto-15α-hydroxy-16,16,19-trimethyl-prost-18-enoic acid, methyl ester.

5. A compound according to claim 2, which is 9-keto-15-hydroxy-15,19-dimethyl-prost-18-enoic acid, methyl ester.

6. A compound according to claim 2, which is 9-keto-15α-hydroxy-16,16,19-trimethyl-prost-18-enoic acid.

7. A compound according to claim 2, which is 9-keto-15β-hydroxy-16,16,19-trimethyl-prost-18-enoic acid.

8. A compound according to claim 2, which is 9-keto-15-hydroxy-15,19-dimethyl-prost-18-enoic acid.

9. A pharmaceutical composition with antiulcer and/or antiasthma activity, comprising as an active principle, a compound according to claim 1, in association with a compatible pharmaceutical carrier.

* * * * *